United States Patent [19]

Means et al.

[11] Patent Number: 4,808,530

[45] Date of Patent: Feb. 28, 1989

[54] PROTEIN IMMOBILIZATION BY ADSORPTION OF A HYDROPHOBIC AMIDINE PROTEIN DERIVATIVE TO A HYDROPHOBIC SURFACE

[75] Inventors: Gary E. Means; Kamaruzaman Ampon, both of Columbus, Ohio

[73] Assignee: The Ohio State University, Columbus, Ohio

[21] Appl. No.: 904,160

[22] Filed: Sep. 5, 1986

[51] Int. Cl.$^4$ .................... C12N 11/08; C12N 11/02; C07K 17/08

[52] U.S. Cl. .................... 435/180; 435/177; 530/815

[58] Field of Search ............... 435/174, 177, 178, 180; 530/815

[56] References Cited

U.S. PATENT DOCUMENTS

| | | | |
|---|---|---|---|
| 3,830,699 | 9/1974 | Zaborsky | 435/181 |
| 3,969,287 | 7/1976 | Jaworek et al. | 435/181 X |
| 4,006,059 | 2/1977 | Butler | 435/179 X |
| 4,267,273 | 5/1981 | Smith | 435/178 X |

OTHER PUBLICATIONS

Wu, et al., Biotech. & Bioeng, vol. XXIII, 1981, pp. 855–861.

Hunter, et al., J. Am. Chem. Soc. vol. 84, 1962, pp. 3491–3504.

*Primary Examiner*—David M. Naff
*Attorney, Agent, or Firm*—Frank H. Foster

[57] ABSTRACT

Immobilization of biologically active protein is carried out by reacting the protein with an imidoester or imidothioester having a hydrophobic moiety to form a hydrophobic amidine derivative of the protein, and then adsorbing the protein derivative to a hydrophobic surface. The protein can be an enzyme such as trypsin and the hydrphobic surface can be a synthetic organic polymer.

19 Claims, No Drawings

PROTEIN IMMOBILIZATION BY ADSORPTION OF A HYDROPHOBIC AMIDINE PROTEIN DERIVATIVE TO A HYDROPHOBIC SURFACE

This invention relates to attaching a biologically active protein to a hydrophobic support. More particularly, it concerns a biologically active protein (e.g. enzyme) attached by adsorption and noncovalent interaction to a hydrophobic polymer, and a preparation involving an amidination of the protein by an imidoester or imidothioester, which includes a highly hydrophobic moiety, which subsequently by adsorption and noncovalent interaction is attached to the hydrophobic polymer.

BACKGROUND

Immobilization can be defined as association of a substance, being immobilized, with another substance, generally termed a support or carrier, so that the associated (i.e. immobilized) substance retains activity and remains substantially associated during the course of chemical processing in which it may be used. Immobilized biologically active proteins, such as antibodies, antigens, enzymes and the like, are highly useful when the association is long lasting and the activity of the biologically active protein is not significantly decreased by its immobilization. Among the reasons for immobilizing a biologically active protein, a most common one is simply to facilitate its recovery or separation from a product prepared by using the protein. Other reasons include: those of ease of reactivating of the protein, should it become deactivated during use; ability to repeatedly reuse it in subsequent processes so long as adequate activity is retained; ability to employ the immobilized protein for continuous processing; and the like.

The art teaches a variety of manners for immobilization, as well as various substances including crushed red brick, porous ceramics, glass beads, wood chips, paper, polymeric resins, and the like, which serve as the support or carrier. These support or carrier materials generally are insoluble materials in the form of solids or gels to facilitate, such as by filtering, centrifuging, precipitation and the like, their separation along with their associated substances from the processing medium in which they provided their chemical function, such as serving as a catalyst. Art taught immobilizations, include encapsulation of the protein with diffusion of reactants and products through an encapsulating membrane. Other art techniques include: entrapment in polymeric gels; cross-linking with bifunctional agents to provide large enough agglomerates enabling separation from liquid mediums; and most frequently chemical attachment, such as by covalent linkage, to the support or substrate. Another technique is an adsorption of the biologically active protein to a solid support or carrier. Each of the foregoing manners and techniques provides some advantages and suffers from some disadvantages.

Probably the simplest and most economical manner is the last-mentioned of adsorption to a solid support. Most biologically active proteins usually are hydophilic or at most weakly hydrophobic and do not adsorb strongly to the most widely used supports. In the absence of strong adsorption, the adsorbed product is not stable with weakly adsorbed protein being lost, such as washed away and/or carried along with the medium, containing product, and with difficulty of separation of the product therefrom. Improvements in attachment of biologically active proteins to hydrophobic carriers by adsorption and noncovalent interaction are highly desirable.

It is now generally known that hydrophobic "pockets" or "patches" are present on the surfaces of most proteins ("The Hydrophobic Effect", C. Tanford, (1980) Wiley-Interscience, N.Y., N.Y.). Proteins differ in their sizes, shapes and number of such patches. Their affinities for hydrophobic materials, thus, also differ and this has been exploited for their separation and purification from each other by a technique called "hydrophobic chromatography". For proteins with a substantial amount of hydrophobic surface area, adsorption to a hydrophobic support can be very strong, in some cases so strong that they cannot effectively be removed even upon washing with high concentrations of organic solvents (L. G. Butler, "Arch. Biochem. Biophys." 171 (1975), 645–650; K. D. Caldwell et al. "Biotechnol. Bioeng." 17 (1975) 613–616). It has been observed that many enzymes retain all or most of their catalytic activity when adsorbed in this manner and this observation has been exploited to prepare immobilized forms of some of these enzymes (Butler, supra). This approach is limited, however, since most enzymes and other proteins are hydrophilic or weakly hydrophobic and do not adsorb strongly to such supports. Some can be immobilized in this manner but gradually leach away in the course of their use.

In 1981, H. Wu and G. E. Means ("Biotech. Bioengr." 23 (1981), 855–861) described a procedure related to that of this invention but differing in a number of important ways. The type of reagent differs, that is, hydrophobic aldehydes plus NaBH$_3$CN, and reactions were conducted in the presence of a support. The present invention overcomes disadvantages of that procedure.

This invention's method differs from those now used for conventional enzyme immobilization. A typical art method involves a step or series of steps to introduce a reactive group onto the support, followed by a step wherein the enzyme and activated support are allowed to react (K. Mosbach, "Methods in Enzymology", 44 (1976), Academic Press, N.Y., N.Y.). The enzyme is attached to the support in such cases, by one or more covalent bonds. The reaction between the soluble protein and a reactive group on an insoluble surface is, however, inherently quite inefficient and this is the source of many problems for such methods. The procedures necessary to introduce a reactive group onto a support are generally expensive and greatly limit the types of support that can be used.

The present invention increases the hydrophobicity of proteins by mild, selective chemical modification in order to strengthen their adsorption onto insoluble hydrophobic surfaces. This approach is applicable to attach a large number of enzymes and other biologically active proteins to a wide variety of hydrophobic materials with the products having important commercial applications.

The present invention involves derivatization of the protein by a relatively inexpensive, soluble reagent. Because both the protein and the reagent are in solution, the reaction is relatively efficient and reaction parameters are easy to control. The modified protein derivative can be isolated and characterized by procedures normally applicable to other soluble proteins. Because the reagents used are analogs of reagents widely used for protein modification, some knowledge exists relative to possible reactions with proteins (G. E. Means and R. E. Feeney, "Chemical Modifications of Protein", (1971), Holden-Day, San Francisco, Calif.). Another step of the procedure involves adsorption to the selected support and resembles procedures described for certain "naturally" hydrophobic proteins.

SUMMARY DISCLOSURE OF INVENTION

The invention's biologically active protein composition attached hydrophobically consists essentially of: (a) a hydrophobic surface; and adsorbed thereon through noncovalent interaction thereto, (b) a hydrophobic moiety R of an imidoester derivative (e.g. amidine) of the structure

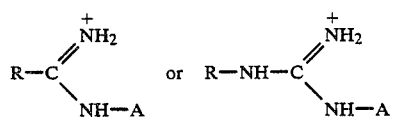

wherein R is selected from the group of hydrophobic moieties consisting of aryl, alkylaryl, arylalkyl, arylalkyloxyethylene ethers, alkyl, and cycloalkyl, and A is a biologically active protein less at least one primary amine group with said primary amine group providing the -NH- connected to A in the foregoing structure. Most desirably, the hydrophobic surface is a synthetic organic polymer whose surface is in the form of a macroreticular adsorbent. Synthetic polymers having monomeric repeating units alike (e.g. aryl and aryl) or resembling (e.g. aryl and arylalkyloxyethylene ethers) the hydrophobic moiety (R) of the imidoester also are desirable. By employing a macroreticular form of the synthetic organic polymer, large surface areas possessing hydrophobicity are available and thus large amounts of the imidoesterprotein derivative may be adsorbed. Particularly preferred for the biologically active protein are enzymes having known value in commercial chemical processes.

The invention includes an immobilized biologically active protein composition comprising: (a) a protein derivative which consists essentially of a biologically active protein containing at least one amino group transformed into an amidino function to which is linked covalently a hydrophobic moiety; and (b) a synthetic organic polymer possessing a hydrophobic surface onto which is adherently adsorbed through noncovalent interaction the hydrophobic moiety of said protein derivative.

To prepare the invention's biologically active protein attached via strong hydrophobic interactions, and thus to immobilize a biologically active protein by noncovalent adsorption to a hydrophobic surface, one proceeds as follows: First, one prepares, purchases, or otherwise provides a requisite imidoester or imidothioester. Useful requisite imidoester or imidothioesters have the structures

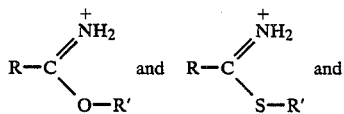

-continued

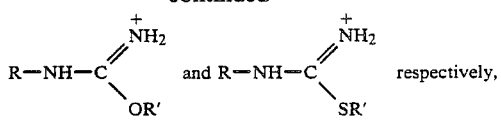 respectively, wherein R is selected from the group of hydrophobic moieties consisting of aryl, alkylaryl, arylalkyl, arylalkyloxyethylene ethers, alkyl, and cycloalkyl, and R' is a lower alkyl radical, such as methyl, ethyl, propyl, etc., containing no more than six carbon atoms. Next, the imidoester or imidothioester is reacted with a biologically active protein containing at least one primary amine group to provide a proteinaceous derivative thereof in which derivative most desirably the foregoing hydrophobic R is a terminal moiety, or at least a protuding side chain moiety, facilitating its contacting with the hydrophobic surface. This reaction with the protein may be deemed an amidination and the reaction products may be called amidino proteins. Where the employed protein is of a structure comprising more than one primary amine group, the reacting is such that at least one of the protein's amino groups is converted to a monosubstituted amidino group. Subsequently, then one contacts the prepared proteinaceous derivative, now containing an enhanced hydrophobic moiety and also generally without perturbation and with, most desirably, the same or closely comparable electronic charged proteinaceous structure compared to the initial protein with the hydrophobic surface under conditions providing noncovalent adsorption of the derivative thereto. Advantageously one may employ an appropriately buffered aqueous medium in this contacting to provide noncovalent adsorption.

DETAILED DISCLOSURE OF INVENTION

Actual and potential commercial utility of immobilized biologically active proteins can be illustrated by mention of a few uses of some immobilized enzymes, although those mentioned are intended to be merely representative and illustrative only and not to exclude other uses and other immobilized biologically active proteins and their uses. Immobilized glucose isomerase is used to convert corn-derived glucose into high-fructose corn syrup for use in soft drinks and other products. Immobilized aminocylase has been used to resolve racemic mixtures. Immobilized penicillin acylase finds utility in preparing synthetic antibiotic precursors. Immobilized lactase converts lactose from whey to glucose and galactose. Immobilized cholinesterase may serve as a pesticide detector; immobilized asparaginase may be used to treat certain forms of leukemia; immobilized antibodies or antigens can be employed in various immunoassays; to mention only a few. Presently, a large market exists and an even larger potential market is forseeable. For example, there is a very large potential market for both home and clinical diagnostic systems involving antibodies/antigens/enzymes attached to solid and/or insoluble supports.

Of concern to the invention are proteins, which are complex nitrogenous organic substances which form an important part of animal and vegetable tissue and are recognized in the art as being proteins. Of proteins the invention is concerned with those which are "biologically active". Biologically active proteins are those that retain their natural or biologically endowed conformations and properties including; for enzymes, catalytic activity; for antibodies, the ability to combine specifically with their antigens; for antigens, the ability to combine with their specific antibodies; for lectins, the ability to combine with the specific carbohydrate moieties, etc. Additionally for purposes of the invention of concern are those biologically active proteins whose structure comprises at least one primary amine group, i.e. $-NH_2$. Exemplary and illustrative biologically active proteins include the following: Enzymes including trypsin, alcohol dehydrogenase, asparaginase, amino acid acylase, glucose isomerase, glucose oxidase, penicillin acylase, alkaline phosphatase, and the like; antibodies including anti-alpha fetoprotein, anti-chorionic gonadotropin, anti-hepatitis B surface antigen, anti-human leukemia and melanoma-associated antigens, and the like; antigens including carcinoembryonic antigens, alpha1-microglobulin antigen, hepatitis B surface antigen, and antigens associated with melanoma, leukemia and immune deficiency syndrome, and the like; and lectins, including concanavalin A and other agglutinins from various plant sources, and the like.

The invention concerns attachment to a hydrophobic carrier or support by adsorption and, in general, is considered applicable to any and all hydrophobic supports recognized in the art as useful for the adsorption thereto of biologically active proteins. A partial listing of useful supports include: carbon; phenoxyacetyl cellulose; cellulose acetate; hydrophobic derivatives of porous glass or silica gel; phenolic polymers; silica gel; cross-linked polystyrene structures; cross-linked polyacrylate and cross-linked polymethacrylate structures; polyvinyl chloride; additional synthetic polymers; and the like. Of particular concern and preferred for the hydrophobic support are those which are synthetic organic polymers. Especially preferred are those which include a monomeric repeating unit alike or closely resembling a hydrophobic portion of the material to be adsorbed.

The support or carrier can present its hydrophobic surface for adsorption thereto in any of numerous forms such as a film, sheet, vessel, surface, pellets, etc., but desirably is porous in nature with porous beads and the like especially preferred.

As representative of useful hydrophobic synthetic organic polymer in the form of porous beads, one can prepare a macroreticular organic resin structure of porous beads by a procedure involving polymerizing monomers that can crosslink in the presence of a phase separating or phase extending solvent system that is miscible with the monomers but that does not dissolve the crosslinked polymer. Normally these polymerizations are carried out by a suspension method, i.e. the monomer and the solvent are dispersed as discrete drops in water and the polymerization is initiated. As polymerization proceeds, the polymer that forms is insoluble in the continuous solvent/monomer phase and precipitates out of solution. In the droplet, microparticles of resin form and become cemented together into a well defined pore structure. In this manner there have been prepared synthetic organic polymers in from 20 to 50 mesh, as hard spherical beads possessing porosity. By controlling monomers and solvent systems, a wide range of porous bead products are preparable. Well known and commercially available are porous beads of nonionic adsorbent polymers including one based on a cross-linked polystyrene structure and another based on a crosslinked polymethacrylate structure. (U.S. Pat. No. 3,531,463, R. L. Gustafson; U.S. Pat. No. 3,663,467, R. L. Albright; "J. Polym. Sci." (1968) 6 pp. 2689–2701, K. A. Kun and R. Kunin).

To increase the hydrophobicity of the biologically active protein by its amidination before its attachment by adsorption and noncovalent interaction to a hydrophobic surface or substrate, one needs to procure, purchase, prepare or otherwise provide a requisite imidoester or imidothioester. Subsequently, the imidoester or imidothioester is reacted with the protein to provide a protein derivative (i.e. amidinate) having a hydrophobic moiety introduced thereto by the imidoester or imidothioester reactant, and then this protein derivative is adsorbed onto the hydrophobic surface or substrate.

Art teachings are available for preparing some useful imidoesters and imidothioesters. Useful imidoesters or imidothioesters have the structures

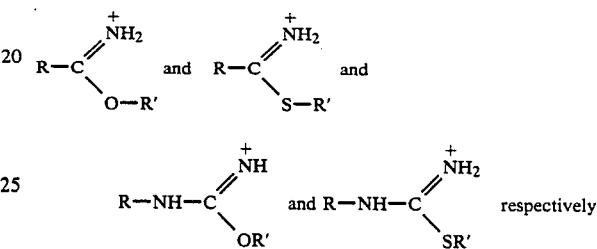

respectively wherein R is selected from the group of hydrophobic moieties consisting of aryl, alkylaryl, arylalkyl, arylalkyloxyethylene ethers, alkyl, and cycloalkyl, and R' is a lower alkyl radical, such as methyl, ethyl, propyl, etc., containing no more than six carbon atoms. As early as 1892 Pinner studied the preparation and reactions of imidoesters. More recent teachings and reviews can be found, for example, in Chem. Revs., 35, 351, (1944), R. L. Shiner and F. W. Neurmann, and J. Am. Chem. Soc., 61, 179, (1961), R. Roger and D. G. Neilson.

Although several preparation routes are available for preparing imidoesters and imidothioesters for use in the invention, a particularly useful general technique is illustrated by specific examples which follow shortly. This general technique proceeds from an alcohol, which includes a requisite hydrophobic R moiety, with the alcohol being cyanoethylated with acrylonitrile in the presence of a base catalyst. Alternately, one starts with the appropriate nitrile, which includes a requisite hydrophobic moiety. In either instance, the next step converts the cyanoethylated alcohol or the R-nitrile, to its corresponding imidoester by reacting with an anhydrous lower alkyl alcohol (e.g. methanol) in the presence of HCl at low temperature according to Pinner's general teachings. Other art techniques and procedures with and without variations may be used to provide useful imidoesters and imidothioesters. Illustrative, representative and typical imidoesters and imidothioesters useful in the invention include: methyl benzimidate hydrochloride, methyl 3-phenylpropionimidate hydrochloride; methyl 4-phenylbutyrimidate hydrochloride; methyl 3-(2-phenoxyethylene)-oxypropionimidate hydrochloride; methyl 4-phenylbenzimidate hydrochloride; methyl n-dodecanimidate hydrochloride; methyl 3-phenylpropionthioimidate hydrochloride; methyl 4-phenyl butyrthioimidate hydrochloride; O-methyl-N(3-phenylpropyl)isourea hydrochloride; and the like.

Derivatization of the biologically active protein; i.e. amidination of the protein, can be accomplished by any of various known art procedures. Note, for example: "J.

Am. Chem. Soc.", M. J. Hunter and M. L. Ludwig, 84, (1962), p. 3491-3504.

Derivatization or amidination of the protein proceeds through reaction of the protein's primary amine group or groups with the oxy-R' or thio-R' function of the imidoester or imidothioester, respectively, to provide a corresponding amidine. Where a protein contains more than one primary amine function, amidination may proceed at more than a single amine function and multiple amidino group may be present after amidination. Amidines, containing introduced multiple amidino groups are useful, but only one amidination or introduction of at least one amidino group is needed to significantly enhance the hydrophobicity of the biologically active protein for purposes of the invention. Substantial activity of the biologically active protein has been found to be retained, in the order of 80% retained activity, with up to 8 to 10 amidino groups formed upon derivatizing the protein.

Illustrative of a useful derivatization or amidination technique is to react the biologically active protein with the requisite imidoester or imidothioester in an alkaline aqueous medium appropriately buffered, depending on the particular protein. Generally the protein in aqueous solution is present in an amount of only one percent or less by weight in the aqueous medium, and the imidoester or imidothioester is employed in a multiple molar amount, e.g. 15-20 moles per mole of amino group in the protein. Known buffers are used and selected so as not to inactivate the protein being amidinated or to interfere with the amidination reaction. After an appropriate reaction time, the derivatization is terminated by acidification, e.g. adding HCl, and the product mixture cleaned up by removal of byproduct(s), for example methanol removal where a reactant used was a methyl imidate. This clean-up or product purification may be by any of several art techniques selected and used based on the byproducts produced e.g. hydrolysis byproducts, by means such as dialysis, ultrafiltration, adsorption chromatography, exclusion chromatography, ion-exchange chromatography, and the like, so long as the activity of the derivative's protein moiety is not significantly affected.

The prepared protein derivative, or amidine, of the protein and imidoester or imidothioester then is ready for immobilization by adsorption and noncovalent interaction with the hydrophobic support or substrate, desirably a synthetic polymer. In general, the immobilization procedure is relatively simple with the protein derivative in aqueous medium brought in contact with the support or substrate, such as by adding to and stirring with an aqueous suspension of synthetic polymeric porous bead adsorbents, for an appropriate time. Contacting time can range from a few minutes to up to several hours, with little additional adsorption occurring upon more prolonged contacting. The contacting must not be by too violent a means, e.g. use mild or gentle stirring, so that the derivative is able to be adsorbed without being dislodged by any violent forces of the contacting. It is within the skill of one in the art to perform several experimental immobilizations to determine and select an appropriate duration for contacting as well as a contacting technique which is not too violent. Generally useful times include from about 30 minutes to 2 hours. Following the contacting, the aqueous medium employed is decanted, drained or otherwise removed from the product of the amidino protein now hydrophobically adsorbed on the surface or support, and this product washed or the like to remove non-bound and weakly bound amidino protein. Thereafter conventional means and techniques can be used to measure the amount of immobilized protein as well as the activity of the immobilized protein compared to non-immobilized protein.

To illustrate the invention by examples, a number of imidoesters and imidothioesters were prepared or otherwise obtained and subsequently employed to provide immobilized biologically active proteins. In general, synthesis of the imidoesters from their corresponding nitriles was accomplished according to Pinner's method (M. J. Hunter & M. L. Ludwig, "J. Am. Chem. Soc."84 (1962) 3491-3504) and is described below. Products were dried over calcium sulfate and sodium hydroxide pellets in vacuo. Melting points were determined in open capillary tubes using Electrothermal Melting Point Apparatus. Nuclear magnetic resonance (nmr) spectra were recorded on a 60 MHz instrument using tetramethylsilane as a reference. Infra-red (ir) spectra were recorded on a Varian instrument (NaCl plates).

EXAMPLE A

Methyl Benzimidate Hydrochloride, $C_6H_5CN^+H_2OCH_3Cl^-$

Benzonitrile (5 g, 0,05 mol) was mixed with absolute $CH_3OH$ (2.4 g, 0.075 mol) and cooled to 0° C. Dry HCl gas (2.8 g, 0.075 mol) was added and the solution was stirred for 30 minutes. Crystallization began after 3 hrs at 4° and continue for 2 more days. Absolute diethylether (100 ml) was added, and the white crystals were collected by filtration, washed with ether and dried to give 7.8 g (91%) of product; mp 103°–105° C.; ir 1630 cm$^{-1}$(C=N).

EXAMPLE B

Methyl-3-PhenylPropionimidate Hydrochloride, $C_6H_5CH_2CH_2CN^+H_2OCH_3Cl^-$

Dry HCl gas (2.8 g, 0.075 mol) was dissolved in dry absolute $CH_3OH$ (2.4 g, 0,075 mol) at −40° C. or below. Hydrocinnamonitrile (5.65 g, 0.05 mol) was added to the cooled solution and stirred for 30 minutes. The solution was warmed up to 0° C. in an ice bath and stirred for 1 hour. Crystallization began after standing overnight at 4° C. and was continued for 2-3 days. Absolute ether (100 ml) was added, the white solid was ground with a pestle and mortar under ether, filtered, washed with more ether and dried in vacuo to give 8.9 g (89%) of product; mp 76°–78°; ir1775cm$^{-1}$− (C=N); nmr (Me$_2$SO-d$_6$) δ4.10(s,OCH$_3$).

EXAMPLE C

Methyl 4-PhenylButyrlimidate Hydrochloride, $C_6H_5(CH_2)_3CN^+H_2OCH_3Cl^-$

Dry HCl gas (2.8 g, 0,075 mol) was dissolved in dry absolute methanol (2.4 g, 0.075 mol) at −40° C. or below. 4-phenylbutyronitrile (7.26 g, 0.05 mol) was added to the cooled solution and stirred for 30 minutes. The solution was gradually warmed up to 0° C. in an ice bath and stirred for 1 hour, and left to stand in the cold room. Crystallization began after standing 2-3 days. About 100 ml of diethylether was added, the white solid was ground under ether, filtered and washed with more ether. The powdered imidoester was dried in vacuo to give 11 g (90%); mp 107-108 1° C.; ir 1665-1670cm$^{-1}$(C=N); nmr(Me$_2$SO-d$_6$)δ4.08(s,OCH$_3$).

EXAMPLE D

Methyl 3-Phenoxyethyleneoxypropionimidate Hydrochloride,
$C_6H_5(OCH_2CH_2)_2-CN^+H_2OCH_3Cl^-$ This was prepared from 2-phenoxyethanol in two steps: firstly, cyanoethylation of 2-phenoxyethanol with acrylonitrile to form $C_6H_5(OCH_2CH_2)_2-CN$ and, secondly, transforming the latter nitrile to the corresponding imidoester by the Pinner synthesis.

Firstly, Cyanoethylation of 2-Phenoxyethanol(Bruson, U.S. Pat. No. 2,280,792)

To a solution of 1.51 g Triton B in 34.5 g 2-phenoxyethanol was added gradually during 30 minutes 13.25 g of acrylonitrile while the reaction was stirred and cooled to 25°-30° C. The mixture was then stirred an additional 4 hrs at 25°-30° C., acidified with dilute HCl, washed with 25 ml of distilled water and the oil layer separated and distilled in vacuo. The desired product $C_6H_5(OCH_2CH_2)_2CN$ distilled over at 103°-105° C. at 0.4 mm Hg. About 24.3 g (51%) of nitrile was collected. (ir(C≡N): 2270 cm$^{-1}$).

Secondly, Preparation of imidate derivative of $C_6H_5(OCH_2CH_2)_2CN$

Dry HCl gas (2.74 g, 0.075 mol) was bubbled into dry MeOH (2.4 g, 0.075 mol) at −40° C. or below. The nitrile (9.56 g, 0.05 mol) was added to the cooled solution and stirred for 30 minutes. The solution was warmed up to 0° C. in an ice bath, stirred for an additional hour and left to stand in the cold room. Crystallization began after standing in the cold overnight and continue for 2-3 days. Dry ethylether (100 ml) was added to extract the crystals, the powder was ground in a mortar, filtered and washed with more ether. The product was dried in vacuo to give 9.8 g (87%); mp 80°-81° C.; ir 1670 cm$^{-1}$ (C=N); nmr(Me$_2$SO-d$_6$)δ4.1(s,OCH$_3$).

EXAMPLE E

Methyl 4-Phenylbenzimidate Hydrochloride, $C_6H_5C_6H_4CN^+H_2OCH_3Cl=$

Dry HCl gas (2.8 g, 0.075 mol) was dissolved in dry absolute methanol (2.4 g, 0,075 mol) at −40° C. or below. 4-Biphenyl-carbonitrile (8.96 g, 0.05 mol) was added to the cooled solution and stirred for 30 minutes. The solution was gradually warmed to 0° C. in an ice bath, stirred for 1 hr. and left to stand in the cold room (4° C.). Crystallization began after standing overnight at 4° C. and continued for 2-3 days. About 100 ml of ether was added, the white solid was ground under ether with a pestle and mortar, filtered, washed with more ether and dried in a vacuum desiccator to give 10.6 g. (86%) of products; mp. 220°-223° C.; ir: 1630-1640 cm$^{-1}$ (C=N), 3400 cm$^{-1}$ (=NH);

EXAMPLE F

Methyl n-Dodecanimidate Hydrochloride:$CH_3(CH_2)_{10}CN+H_2OCH_3Cl-$Dry HCl(2.8 g, 0.075 mol) was dissolved in a mixture of methanol (2.4 g, 0.075 mol) and 15 ml absolute ether at −40° C. or below. n-Undecylcyanide (9.1g, 0.05 mol) was added directly to the cooled ethereal mixture and stirred. Ether was added prior to the addition of nitrile in order to prevent the rapid solidification of the reaction mixture (Mc.Elvain and Nelsion, 1942, J. Am. Chem. Soc. 64 1825-1830). Solidification of the reaction mixture began after about 5-10 minutes. It was left to stand at 0° C. for 2 hours. Next, 100 ml of ether was added, the white solid was ground with a pestle and mortar, filtered, washed with more ether and dried in a vacuum desiccator to give 9.5 g (89%) of product; mp. 97°-98° C.; ir. 1640-1650 cm$^{-1}$(C=N), 3380 cm$^{-1}$(=NH);

EXAMPLE G

Methyl 4-octylphenyldi(oxyethylene)oxypropyleneimidate Hydrochloride,
$4-(C_8H_{17})C_6H_4(OCH_2CH_2)_3-CN^+H_2OCH_3Cl-$ The synthesis was accomplished by a sequence of reactions. In the first reaction $4-(C_8H_{17})C_6H_4(OCH_2CH_2)_2OH$ (36.81 g, 0.125 mol) was cyanoethylated with acrylonitrile (6.63 g, 0.125 mol) in the presence of a base catalyst, Triton B (1.511 g) essentially according to the method of Bruson, U.S. Pat. No. 2,280,792 (1949). Completion of the reaction was monitored by the disappearance of the OH and the appearance of the CN absorbance in the product using the ir spectrophotometer. More acrylonitrile was added to complete the reaction because it is not possible to distill off the product from the reaction mixture under vacuum. About 34 g (78%) of nitrile (not pure) was obtained.

The nitrile (17.37 g, 0.05 mol) was converted to the corresponding imidoester by the Pinner synthesis (Hunter and Ludwig, supra) in the presence of MeOH (2.4 g, 0.075 mol) and dry HCl (2.74 g, 0.075 mol). The imidoester hydrochloride is a viscous, yellowish liquid much thicker than the starting material and no crystals precipitate out even after standing for 2-3 days in the cold room. The characteristic ir(C=N) stretching band of the original nitrile between 2200-2300 cm$^{-1}$ disappeared, and was replaced by the CH$_3$ stretching of OCH$_3$ at 1740 cm$^{-1}$, ir(C=N) at 1650-1700 cm$^{-1}$ and the ir(NH) stretching at 3200-3370 cm$^{-1}$.

Thioimidates

If appropriate thioimidates for practice of the invention are not readily available from commercial sources, they may be prepared as desired. For example, thioimidates can be synthesized from appropriate nitriles and thiols by the Pinner Synthesis as follows: (Roger, R., and Neilson, D. G. (1961) "Chem. Revs.", 61 on 179-211;

Mull, R. P. (1965) U.S. Pat. No. 3,189,601;

Mager, R., Scheithauer, S., and Kunz, D. (1966) Chem. Ber., 99, 1393-;

Behringer, H., and Weber, D. (1965) Ann. Chem., 682, 196-;

$$RCN + R'SH + HCl \longrightarrow R-C\overset{\displaystyle NH_2}{\underset{\displaystyle SR'}{\diagup\!\!\!\!\!\diagdown}} + Cl^-$$

Additionally, they may be prepared from thioamides by direct alkylation at the sulfur atom with alkyl halides (Walter, W., and Voss, J. (1970) "The Chemistry of Amides"ed. J. Zabicky, Interscience Publishers, New York pp. 383-475).

$$R-C\overset{\displaystyle S}{\underset{\displaystyle NH_2}{\diagup\!\!\!\!\!\diagdown}} + R'I \xrightarrow{-HI} RC\overset{\displaystyle NH}{\underset{\displaystyle SR'}{\diagup\!\!\!\!\!\diagdown}}$$

thioamides    thioimidates

The thioamides may be prepared by addition of $H_2S$ to a nitrile group (Walter and Voss, 1970) or $$R-C\equiv N + H_2S \longrightarrow R-\underset{\underset{\displaystyle S}{\|}}{C}-NH_2$$

by thiolysis of amidines and imidic esters.

$$R-CN \xrightarrow[HX]{R'NH_2} R-\underset{\underset{\displaystyle NH}{\|}}{C}-NHR' \xrightarrow[Pyridine]{H_2S}$$

$$R-\underset{\underset{\displaystyle S}{\|}}{C}-NHR' + R-\underset{\underset{\displaystyle S}{\|}}{C}-NH_2$$

EXAMPLE H

Methyl 3-Phenylpropionthioimidate Hydrochloride, $C_6H_5CH_2CH_2CN + H_2SCH_3Cl-$ By following the just-mentioned teachings for preparing thioimidates, there is prepared Methyl 3-Phenyl-Propionthioimidate Hydrochloride.

EXAMPLE I

Methyl 4-PhenylButyrlthioimidate Hydrochloride, $C_6H_5(CH_2)_3CN + H_2SCH_3Cl-$ By following the just-described teachings for preparing thioimidates, there is prepared Methyl 4-Phenyl Butyrlthioimidate Hydrochloride.

N-Alkylisoureas

If appropriate alkylisoureas for practice of the invention are not readily available from commercial sources, they may be prepared as desired. For example, O-alkylisoureas may be prepared by the reaction of corresponding carbodiimides with alcohols (Williams, A., and Ibrahim, I. T. (1981) "Chem. Rev.", 81, 589-636)

$$R-N=C=N-R' + R''OH \longrightarrow R-NH-C\overset{\displaystyle NR'}{\underset{\displaystyle OR''}{\diagup\!\!\!\!\!\diagdown}}$$

This reaction is carried out with the alkoxide, (Davies, A. G., and Puddephatt, R. J. (1968) "J. Chem. Soc. C", 1479), without catalyst (Markiw, R. T. and Canellakir, ES, 1969, "J. Org. Chem.", 34, 3707) and with copper salts as catalyst (Vowinkel, E. and Gleichenhagen, P. (1974) "Tetrahedron Lett"., 143., Dawson, B. A., and Gurbaxani, S. 1973, "J. Org. Chem."38, 1051.

The carbodiimides are prepared from corresponding ureas or thioureas (Williams, A. and Ibraham, I. T. (1981) "Chem Revs." 81, 589-636).

EXAMPLE J

O-Methyl-N-(3-Phenylpropyl) isourea $C_6H_5(CH_2)_3NHCN + H_2OCH_3$

By following the just-presented teachings for preparing alkylisoureas, there is prepared O-Methyl-N-(3-Phenylpropyl)isourea.

N-Alkylisothioureas

If appropriate alkylisothioureas for practice of the invention are not readily available, they may be prepared as desired. For example, reaction of appropriate carbodiimide with thiols may be used to prepare S-alkyl or S-arylisothiourea directly.

$$R-SH \xrightarrow[2.\ (CO_2H)_2]{1.\ R'NC\equiv NR'} R'NH-C\overset{\displaystyle NR'}{\underset{\displaystyle SR}{\diagup\!\!\!\!\!\diagdown}} + HC_2O_4^-$$

(Vowinkel, E. and Claussen, G. (1974) "Chem. Ber.", 107, 898 (Williams, A., and Ibrahim, I. T. (1981) "Chem. Rev."81, 589-636).

The isothiourea derivatives may be conveniently isolated as the oxalate salts.

EXAMPLE K

S-Methyl-N-(3-Phenylpropyl)isothiourea Hydrochloride $C_6H_5(CH_2)_3NH-CN + H_2SCH_3Cl-$ By following the just-described teachings there is prepared S-Methyl-N-(3-Phenylpropyl)-isothiourea Hydrochloride.

Each of the imidoesters and imidothioesters, prepared as described in the preceding lettered examples, and some otherways obtained, are employed to amidinate at least one or more biologically active proteins. To further illustrate the invention a number of examples of these amidinations of proteins follow:

EXAMPLE 1

Generally the derivatization or amidination of various proteins with various imidoesters is accomplished according to the procedure of Hunter and Ludwig (1962) supra, such as follows for trypsin:

$$\text{Protein-NH}_2 + R-\overset{+}{C}NH_2OCH_3.Cl^- \longrightarrow$$

$$R-\underset{\underset{\displaystyle NH-Protein}{|}}{\overset{+}{C}NH_2} + CH_3OH$$

Several small additions (5-10 mg each) of the imidoester are made at intervals of about 10 to 20 minutes to a solution of trypsin in 0.1M dimethylaminoethanol buffer pH 9.5 and 20 mM in $CaCl_{12}$ at 0° for 90 minutes. The reaction is terminated by acidification with HCl to pH 3.5 and the derivatized trypsin is passed through a column of Sephadex G-25 equilibrated with $10^{-3}M$ HCl. By the above general procedure bovine trypsin also was derivatized or amidinated by reaction with each of the imidoester prepared in the preceding Examples A, B, C, D, E, F, and G.

EXAMPLE 2

Alcohol dehydrogenase was derivatized or amidinated with the imidoester of Example B, $C_6H_5(CH_2)_2CN^+H_2OCH_3$, and also with the imidoester of Example C, $C_6H_5(CH_2)_3CN^+H_2OCH_3$, according to the general procedure of Example 1.

EXAMPLE 3

Asparaginase was derivatized or amidinated with the imidoester of Example B, $C_6H_5(CH_2)_2CN^+H_2OCH_3$, according to the general procedure of Example 1.

EXAMPLE 4

Aminoacylase was derivatized or amidinated with the imidoester of Example B, $C_6H_5(CH_2)_2CN^+H_2OCH_3$ and also with the imidoester of Example C, $C_6H_5(CH_2)_3CN^+H_2OCH_3$, according to the general procedure of Example 1.

EXAMPLE 5

Alkaline phosphatase was derivatized or amidinated with the imidoester of Example C, $C_6H_5(CH_2)_3CN^+H_2OCH_3$, according to the general procedure of Example 1.

EXAMPLE 6

Immunoglobulin and monoclonal antibodies are derivatized or amidinated with the imidoester of Example C, $C_6H_5(CH_2)_3CN^+H_2OCH_3$, according to the general procedure of Example 1.

EXAMPLE 7

Trypsin is derivatized or amidinated with each of the imidoesters: of Example H, $C_6H_5(CH_2)_3CNH_2SCH_3$, of Example I, $C_6H_5(CH_2)_3CN^+H_2SCH_3$; of Example J, $C_6H_5(CH_2)_3NHCN^+H_2OCH_3$; and also with the imidoester of Example K, $C_6H_5(CH_2)_3$-NH-C-N$^+$H$_2$SCH$_3$; according to the general procedure of Example 1.

Following the derivatization, or amidination, of the various biologically active proteins, such as just described in the arabic-numbered examples, the resulting amidino proteins are immobilized by adsorption and noncovalent interaction onto various hydrophobic carriers and the immobilized proteins evaluated by various techniques such as illustrated by the following examples:

EXAMPLE I

Immobilization of various derivatized trypsins were accomplished as follows: the derivative (from about 2 to 50 mg) was added to porous polymer beads (400 mg dry wt.) in 0.05 M triethanolamine buffer pH 7.5 and 20 mM in $CaCl_2$. The mixture was stirred for 1 to 2 hours at room temperature, the resin was then allowed to sediment and the supernatant was removed. The resin was washed 3 times each with buffered 1M KCl and 50% ethylene glycol, once with 20 ml of distilled water and finally resuspended in 0.05 M triethanolamine buffer pH 7.5.

The hydrolysis of benzoyl arginine ethyl ester by soluble and immobilized trypsins was monitored by the pH-stat method of G. W. Schwert, H. Neurath, S. Kaufman and J. E. Snoke (1948), *J. Biol. Chem.*, 172, pp 221–238, using an automatic titrator. Table 1 shows the results obtained for the immobilized deivative obtained with each of seven different imidoesters. Trypsin active sites also were estimated using the active site titrant nitrophenylguanidinobenzoate [T. Chase and E. Shaw (1967) *Biochem. Biophys. Res. Comm.*, 29, p508–514] and total protein bound was determined by the amino acid analysis after acid hydrolysis.

The following two tables tabulate information concerning the various derivatized trypsins, their immobilizations, activities, etc.

TABLE 1

| Imidoesters Employed for Derivatization | Total Activity Applied (umole/min) | Activity Immobilized (umole/min) | Immobilization yield (%) | Active sites (%) |
| --- | --- | --- | --- | --- |
| Unmodified (none) | 24.8 | 1.80 | 7.3 | 57 |
| (Ex. A) $C_6H_5\text{-}C(=N^+H_2Cl^-)\text{-}OCH_3$ | 24.3 | 6.6 | 27 | — |
| (Ex. B) $C_6H_5\text{-}(CH_2)_2\text{-}C(=N^+H_2Cl^-)\text{-}OCH_3$ | 17.8 | 9.0 | 50.3 | 42.5 |
| (Ex. C) $C_6H_5\text{-}(CH_2)_3\text{-}C(=N^+H_2Cl^-)\text{-}OCH_3$ | 21.5 | 13.6 | 63.3 | 36.9 |
| (Ex. D) $C_6H_5\text{-}(OCH_2CH_2)_2\text{-}C(=N^+H_2Cl^-)\text{-}OCH_3$ | 21.3 | 10.5 | 49.2 | 35.1 |

TABLE 1-continued
Immobilization of Derivatized Trypsin onto Porous Beads* of a Polyacrylate Resin

| | Imidoesters Employed for Derivatization | Total Activity Applied (umole/min) | Activity Immobilized (umole/min) | Immobilization yield (%) | Active sites (%) |
|---|---|---|---|---|---|
| (Ex. E) | phenyl-phenyl-C(=NH$_2$Cl$^-$)OCH$_3$ | 21.0 | 2.5 | 12.0 | — |
| (Ex. F) | CH$_3$—(CH$_2$)$_{10}$—C(=NH$_2$Cl$^-$)OCH$_3$ | 22.2 | 2.8 | 12.6 | — |
| (Ex. G) | C$_8$H$_{17}$—phenyl—(OCH$_2$CH$_2$)$_3$—C(=NH$_2$Cl$^-$)OCH$_3$ | 21.5 | 6.8 | 31.7 | 28.6 |

*Amberlite XAD-7, a crosslinked polymethacrylate resin in bead form possessing a porosity volume of 55%, a surface area of 450 m$^2$/g, an average pore diameter of 90 Å, and a mesh of 20 to 60 (U.S. Sieve Series).

TABLE 2
Amidination of Bovine Trypsin with Various Imidoester

| | Imidoesters Employed For Derivatization | Total Activity (umole/min/mg protein) Before Modification | After Modification | Extent of Modification (%) |
|---|---|---|---|---|
| (Ex. A.) | phenyl-C(=NH$_2$Cl$^-$)OCH$_3$ | 32.3 | 38.3 | 61.4 |
| (Ex. B) | phenyl-(CH$_2$)$_2$-C(=NH$_2$Cl$^-$)OCH$_3$ | 39.8 | 43.0 | 50.0 |
| (Ex. C) | phenyl-(CH$_2$)$_3$-C(=NH$_2$Cl$^-$)OCH$_3$ | 29.5 | 38.0 | 35.5 |
| (Ex. D) | phenyl-(OCH$_2$CH$_2$)$_2$-C(=NH$_2$Cl$^-$)OCH$_3$ | 30.8 | 37.6 | 29.0 |
| (Ex. E) | phenyl-phenyl-C(=NH$_2$Cl$^-$)OCH$_3$ | 47.0 | 36.0 | 23.0 |
| (Ex. F) | CH$_3$—(CH$_2$)$_{10}$—C(=NH$_2$Cl$^-$)OCH$_3$ | 32.6 | 36.9 | 17.0 |
| (Ex. G) | C$_8$H$_{17}$—phenyl—(OCH$_2$CH$_2$)$_3$—C(=NH$_2$Cl$^-$)OCH$_3$ | 28.1 | 29.9 | 15.0 |

EXAMPLE II

The imidoester derivatized trypsins of Examples A through G were immobilized on various solid supports with results shown in the following table 3.

EXAMPLE III

Several enzymes, which had been derivatized or amidinated according to the general procedure of Example I, were immobilized on porous beads of a polyacrylate resin. The following table 4 summarizes and tabulates information on these various enzymes, as well as the various imidoesters used to derivatize the various enzymes and the enzyme derivative activities before and after their immobilizations.

TABLE 3

Immobilization of Imidoester Derivatized Trypsin on Various Solid Supports

| Imidoesters (Employed for Derivatization) | Immobilization yield (%)[i] | | | |
|---|---|---|---|---|
| | XAD-7[a] | XAD-2[b] | SVB[c] | IR-120 PLUS[d] |
| (Ex. A) C$_6$H$_5$—C(=NH$_2$Cl$^-$)(OCH$_3$) | 17–27 | 0 | 0 | 0 |
| (Ex. B) C$_6$H$_5$—(CH$_2$)$_2$—C(=NH$_2$Cl$^-$)(OCH$_3$) | 50.3 | 8–15 | 8 | 3 |
| (Ex. C) C$_6$H$_5$—(CH$_2$)$_3$—C(=NH$_2$Cl$^-$)(OCH$_3$) | 63.3 | 10 | 5–10 | 1 |
| (Ex. D) C$_6$H$_5$—(OCH$_2$CH$_2$)$_2$—C(=NH$_2$Cl$^-$)(OCH$_3$) | 35–50 | 10 | 2 | — |
| (Ex. E) C$_6$H$_5$—C$_6$H$_4$—C(=NH$_2$Cl$^-$)(OCH$_3$) | 12.0 | 1 | 0 | 0 |
| (Ex. F) CH$_3$—(CH$_2$)$_{10}$—C(=NH$_2$Cl$^-$)(OCH$_3$) | 12.6 | 1 | 0 | — |
| (Ex. G) C$_8$H$_{17}$C$_6$H$_4$—(OCH$_2$CH$_2$)$_3$—C(=NH$_2$Cl$^-$)(OCH$_3$) | 32 | 7 | 2 | — |

[i]Percent activity of the imidoester derivatized trypsin which is present after the immobilization.
[a]Amberlite XAD-7, a cross-linked polymethacrylate resin in bead form possessing a porosity volume of 55%, a surface area of 450 m$^2$/g, an average pore diameter of 90A*, and a mesh of 20 to 60 (U.S. Sieve Series)
[b]Amberlite XAD-2, a macroreticular styrene divinylbenzene copolymer, with a porosity volume of 42%, a surface area of 300 m$^2$/g, an average pore diameter of 90A*, and a mesh of 20 to 60 (U.S. Sieve Series)
[c]Sorptive polymer - SVB, is a macroreticular styrene-divinylbenzene copolymers with a dry mesh designation of 40 to 100 (Dow Chemical)
[d]Amberlite IR-120 Plus is a strongly acidic cation exchanger of styrene divinyl benzene copolymer, with an effective size of 0.50 mm. This resin was washed and titrated with NaOH to neutralize the negative charge before being used for immobilizing derivatized trypsin.

TABLE 4

Immobilization of Derivatized Bovine Trypsin, Yeast Alcohol Dehydrogenase, E. Coli Asparaginase, Porcine Aminoacylase and Calf Alkaline Phosphatase on Porous Beads* of Polyacrylate Resin

| (Biologically Active Protein) Enzymes | Imidoesters (Employed for Derivatization) | Total Activity Applied (Units**) | Total Activity Immobilized (Units**) | Immobilization Yield (%) |
|---|---|---|---|---|
| Trypsin | Unmodified (none) | 24.8 | 1.8 | 7.3 |

TABLE 4-continued

Immobilization of Derivatized Bovine Trypsin, Yeast Alcohol Dehydrogenase, E. Coli Asparaginase, Porcine Aminoacylase and Calf Alkaline Phosphatase on Porous Beads* of Polyacrylate Resin

| (Biologically Active Protein) Enzymes | Imidoesters (Employed for Derivatization) | Total Activity Applied (Units**) | Total Activity Immobilized (Units**) | Immobilization Yield (%) |
|---|---|---|---|---|
| | Ex. B: Ph—(CH$_2$)$_2$—C(=NH$_2^+$Cl$^-$)OCH$_3$ | 17.8 | 9.0 | 50.3 |
| | Ex. C: Ph—(CH$_2$)$_3$—C(=NH$_2^+$Cl$^-$)OCH$_3$ | 21.5 | 13.6 | 63.3 |
| Alcohol Dehydrogenase | Unmodified (none) | 11.6 | 0.7 | 6.0 |
| | Ex. B: Ph—(CH$_2$)$_2$—C(=NH$_2^+$Cl$^-$)OCH$_3$ | 14.2 | 9.9 | 70.0 |
| | Ex. C: Ph—(CH$_2$)$_2$—C(=NH$_2^+$Cl$^-$)OCH$_3$ | 23.4 | 13.0 | 55.7 |
| Asparaginase | Unmodified (none) | 10 | 0.8 | 8.0 |
| | Ex. B: Ph—(CH$_2$)$_2$—C(=NH$_2^+$Cl$^-$)OCH$_3$ | 10 | 4.8 | 48.0 |
| Amino Acylase | Unmodified (none) | 25.0 | 2.3 | 6.8 |
| | Ex. C: Ph—(CH$_2$)$_3$—C(=NH$_2^+$Cl$^-$)OCH$_3$ | 34.0 | 17.1 | 50.4 |
| Alkaline Phosphatase | Unmodified (none) | 2.72 | 0 | 0 |
| | Ex. C: Ph—(CH$_2$)$_3$—C(=NH$_2^+$Cl$^-$)OCH$_3$ | 2.72 | 0.32 | 12 |

*Amberlite XAD-7, a cross-linked polymethacrylate resin in bead form possessing a porosity volume of 55%, a surface area of 450 m$^2$/g, an average pore diameter of 90A°, a a mesh size of +20 to +60 (U.S. Sieve Series).

**The unit of enzymic activity for the various enzymes was expressed as follows: For trypsin, 1 unit hydrolyses 1 umole of benzoyl arginine ethyl ester (BAEE)/min at 25°, pH 8.2 in the presence of 0.01 M Calcium ion. The hydrolysis of BAEE is measured by the pH-stat method of Schwert et al, 1948, "J. Biol. Chem." 172,221;

For alcohol dehydrogenase, 1 unit coverts 1 umole of NAD+ to NADH per minute at 25° and pH 8.8. The rate of absorbance at 340 nm resulting from reduction of NAD$^+$ is measured by the method of Vallee, B. L., and Hoch, F. L. (1955) "Proc. Nat. Acad. Sci. USA", 41,327

For asparaginase, 1 unit catalyses the release of 1 umole of ammonia/min at 37°, pH 8.6 from asparagine. The rate of hydrolysis of asparagine is determined by measuring the liberated ammonia by the method of Mashburn, L. T., and Wriston, J. C., (1963) "Biochem. Biophys. Res. Comm." 12,50.

For aminoacylase, 1 unit catalyses the hydrolysis of acetyl-L-methionine/min at 25° and pH 7.0. The rate of hydrolysis of AM is measured by the decrease in absorbance at 238 nm (Mitz, M. A., and Schlueter, R. J. (1958) "Biochim. Biophys. Acta", 27,168.)

For alkaline phosphatase, 1 unit hydrolyses 1 umole of p-nitrophenol phosphate/min at 25°, pH 8.0. Hydrolysis of p-nitrophenol-phosphate is measured by the increase in absorbance at 405 (Garen, A., and Levinthal, C., (1960) "Biochim. Biophys. Acta", 38, 470–)

Evaluation was made of the stability of the foregoing described prepared immobilized imidoester derivatized bovine trypsin, yeast alcohol dehydrogenase and E. Coli asparaginase at 4° C. and 23° C. (ambient room temperature) after storage for 30 days. Results of this evaluation follow in Table 5.

TABLE 5

Stability of Immobilized Imidoester Derivatized Bovine Trypsin, Yeast Alcohol Dehydrogenase and E. Coli Asparaginase at 4 and 23° C.

| Immobilized Imidoester Derivatized Enzymes | Residual activities relative to initial after 30 days (%) | |
|---|---|---|
| | 23° C. | 4° C. |
| Trypsin (a) | 75 (after 12 days) | — |
| Control | 0 | — |

TABLE 5-continued

Stability of Immobilized Imidoester Derivatized Bovine Trypsin, Yeast Alcohol Dehydrogenase and *E. Coli* Asparaginase at 4 and 23° C.

| Immobilized Imidoester Derivatized Enzymes | Residual activities relative to initial after 30 days (%) | |
|---|---|---|
| | 23° C. | 4° C. |
| Alcohol Dehydrogenase (b) | 40 | 45 |
| Control | 0 | 0 |
| Asparaginase (c) | 52 | 81 |
| Control | 0 | 20 |

(a) Trypsin was incubated in 0.01 M triethanolamine buffer pH 7.5.
(b) Alcohol dehydrogenase was incubated in 0.01 M phospate buffer pH 6.5 plus 1 mM dithiothreitol.
(c) Asparaginase was incubated in 0.01 M Tris-HCl buffer pH 7.0. Sodium azide (0.1%) was added to each buffer to prevent microbial growth.

Each control was nonimmobilized native enzyme, and otherwise was handled and activity checked the same as the immobilized imidoester derivatized specific enzymes.

Additional data was collected on the stability of the foregoing described imidoester derivatized asparaginase immobilized on Amberlite XAD-7, crosslinked polymethacrylate resin in porous bead form, at 4° C. and 23° C. along with nonimmobilized native asparaginase. A sample of immobilized asparaginase (2-3 mg protein/400 mg dry wt XAD-7) in 0.01 M dimethylaminoethanol buffer pH 8.4 was kept at ambient room temperature (23°) and another in a refrigerator at 4°. The activity was determined at intervals by following the release of ammonia from asparagine by the method of Mashburn et al., (1963), *Biochem. Biophys. Res. Comm.* 12, 50. Native asparaginase similarly incubated was used as a control.

Stability of Immobilized Asparaginase on Amberlite XAD-7 Beads at 4° and 23° C. with Time

| Time Elapsed (Days) | Activity Remaining (%) | | | |
|---|---|---|---|---|
| | Native Asparaginase | | Immobilized Amidinated Asparaginase | |
| | 4° | 23° | 4° | 23° |
| 0 | 100 | 100 | 100 | 100 |
| 2 | — | 38.8 | — | 92 |
| 6 | 73.4 | — | 89.5 | 70.7 |
| 8 | 64.3 | 13.4 | 89.6 | 66.0 |
| 14 | 51.1 | 0.35 | 86.6 | 58.6 |
| 30 | 26.7 | 0 | 80.7 | 51.6 |

For comparison purposes an evaluation was made of the kinetic parameters for the hydrolysis of BAEE (benzoyl-L-arginine ethyl ester.HCl) by soluble native trypsin, soluble amidated trypsin, and amidated trypsin hydrophobically bound to porous beads of polymethacrylate resin. Results follow in Table 7.

TABLE 7

Comparison of Kinetic Parameters for the Hydrolysis of BAEE* by the Soluble Native Trypsin, Soluble Amidinated Trypsin and Amidinated Trypsin Bound to Porous Beads of Polyacrylate Resin**

| Parameters | Trypsin | | |
|---|---|---|---|
| | Soluble Native | Soluble Amidinated | Amidinated and Bound to Porous Beads |
| Km (app) (uM) | 17.8 | 27 | 111-115 |
| pH Optimum | 8.2-8.3 | 8.2-8.3 | |
| Moles active site (a) Mole protein | 0.53 | 0.51 | 0.39 |
| BAEE activity (b) (Molecules/active site/minute) | 1019 | 910 | 870 |

*BAEE is benzoyl-L-arginine ethyl ester.HCl
**Amberlite XAD-7, a crosslinked polymethacrylate resin in bead form possessing a porosity volume of 55%, a surface area of 450 m 2/g, an average pore diameter of 90 A, and a mesh sieve size of 20 to 60 (U.S. Sieve Series).
(a) Active site titrations by method of Chase and Shaw (1967), supra, using p-nitrophenylguanidinobenzoate (NPGB)
(b) 0.01 M BAEE in 1 mM KCl, 5 mM CaCl₂, pH 7.8 24.5° C. in a pH stat.

EXAMPLE IV

Trypsin was derivatized or amidinated according to the general procedure of Example I with each of the imidoesters of Example B and C except for omission of passage through the column of Sephadex. Instead, the prepared amidines were cleaned up by placing in contact with dialysis-grade cellulose acetate membranes with dialysis carried forth for several hours to remove byproducts of the derivatization. Thereafter, the cellulose acetate membrane was washed with distilled water and then with tris buffer (pH 7.5, 0.05 M tris(hydroxymethyl)aminomethane).

Table 8, which follows, presents the results of this example, wherein activities were measured by the pH-stat method of Schwert et al. (supra).

TABLE 8

Trypsin Activity on Cellulose Acetate Membrane

| Imidoesters Employed for Trypsin Derivatization | Activity Adsorbed on Membrane (Units/mg)(a) | Activity Immobilized (Units/mg)(b) |
|---|---|---|
| Control (Unmodified Enzyme) | 0.071 | 0.0128 |
| (Ex. B) 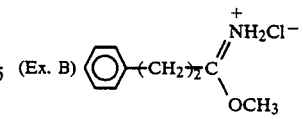 | 0.082 | 0.079 |
| (Ex. C) 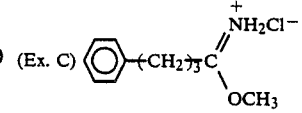 | 0.0594 | 0.0588 |

(a)Determined, after the water/tris buffer washings.
(b)Determined, after the water/tris buffer-washed membrane additionally had been washed with a KCl/ethylene glycol solution and then with water and tris buffer washings.

EXAMPLE V

When the derivatized or amidinated products (i.e. amidino proteins) of Examples 6 and 7 are immobilized by general procedures taught herein so as to be hydrophobically attached to various synthetic polymers, each are found to exhibit a significant immobilization yield (i.e. retain after immobilization a significant portion of the amount of biological activity which they possessed as amidino protein).

It will be appreciated that changes and modifications may be made in the foregoing described embodiments of the invention without departing from the true scope of the invention. Accordingly, the preceding disclosure is to be construed as illustrative and not limiting, with the scope of the invention defined solely by the claims, which follow.

We claim:

1. An immobilized biologically active protein composition consisting essentially of:
   (a) a hydrophobic surface; and adsorbed thereon through hydrophobic and noncovalent interaction thereto,
   (b) a hydrophobic moiety R of a derivative of a biologically active protein of the structure selected from the group consisting of

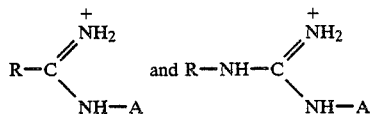

wherein R is selected from the group of hydrophobic moieties consisting of aryl, alkylaryl, arylalkyl, and arylalkyloxyethylene ethers, alkyl, and alkylaryl, arylalkyl, and arylalkyloxyethylene ethers, alkyl, and cycloalkyl, and A is the biologically active protein less at least one primary amine group which provides the -NH- connected to A in the foregoing structure.

2. The composition of claim 1 in which the hydrophobic surface is a synthetic organic polymer.

3. The composition of claim 2 in which said polymer is polystyrene resin in the form of porous beads possessing a macroreticular structure.

4. The composition of claim 2 in which said polymer is a polymethacrylate resin in the form of porous beads possessing a macroreticular structure.

5. The composition of claim 2 in which the biologically active protein is an enzyme.

6. The composition of claim 2 in which the derivative of the biological active protein is a methyl 3-phenypropionimidate derivative of trypsin.

7. An immobilized biologically active protein composition comprising:
   (a) a protein derivative which consists essentially of a biologically active protein containing at least one amino group thereof transformed into an amidino function to which is linked covalently a hydrophobic moiety, said protein derivative having the structure

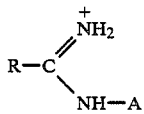

wherein R is the hydrophobic moiety selected from the group of hydrophobic moieties consisting of aryl, alkylaryl, arylalkyl, arylalkyloxyethylene ethers, alkyl, and cycloalkyl, and A is the biologically active protein less the at least one amino group which provides the -NH- connected to A in the foregoing structure; and
   (b) a synthetic organic polymer possessing a hydrophobic surface onto which is adherently adsorbed through noncovalent interaction said hydrophobic moiety of said protein derivative.

8. The composition of claim 7 in which the hydrophobic moiety linked to the amidino function possesses a hydrophobicity greater than that of the -NH$_2$ group.

9. The composition of claim 8 in which the biologically active protein is an enzyme.

10. The composition of claim 9 in which the enzyme is trypsin.

11. A process of immobilization of a biologically active protein by hydrophobic and noncovalent adsorption to a hydrophobic surface, comprising the steps of:
    (a) providing an imidoester or imidothioester of the structure selected from

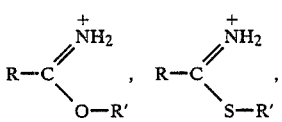

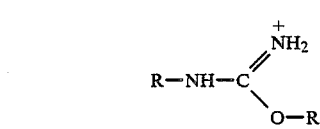

wherein R is a moiety selected for the group of hydrophobic moieties consisting of aryl, alkylaryl, arylalkyl, arylalkyloxyethylene ethers, alkyl, and cycloalkyl and R, is a lower alkyl radical;
    (b) reacting said imidoester or imidothioester with a biologically active protein containing at least one primary amine group to provide a corresponding amidine derivative of the protein; and
    (c) contacting the resulting amidine derivative of the protein with the hydrophobic surface under conditions adapted to provide noncovalent adsorption of the moiety R onto the hydrophobic surface to immobilize said amidine derivative of the protein.

12. The process of claim 11 wherein the hydrophobic surface is provided by a synthetic organic polymer.

13. The process of claim 12 in which said polymer is in the form of porous beads possessing a macroreticular structure.

14. The process of claim 12 in which the step (c) of contacting is conducted in an aqueous medium buffered by a buffer adapted to provide the hydrophobic and noncovalent adsorption to the hydrophobic surface without perturbation of electronic charge distribution present in a biologically active moiety of said derivative of the protein.

15. The process of claim 13 wherein said biologically active protein is provided by an enzyme.

16. The process of claim 15 wherein each enzyme is provided by trypsin.

17. A process of immobilization of a biologically active protein by hydrophobic adsorption, which process comprises:
    (a) contacting in an aqueous medium a protein derivative, which consists of a biologically active protein with at least one amino group thereof transformed into an amidino function to which is linked a hydrophobic moiety, with a hydrophobic surface of a synthetic organic polymer to immobilize the protein derivative by hydrophobic adsorption of the hydrophobic moiety onto the hydrophobic surface, said protein derivative having the structure

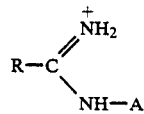

wherein R is a moiety selected from the group of hydrophobic moieties consisting of aryl, alkylaryl, arlalkyl, arylalkyloxyethylene ethers, alkyl, and cycloalkyl, and A is the biologically active protein less the at least one amino group which provides the -NH-connected to A in said structure; and (b) performing said contacting while said aqueous medium contains a buffer adapted to provide the hydrophobic adsorption without perturbation of electronic charge distribution present in a biologically active moiety of said protein derivative.

18. The process of claim 17 wherein the protein derivative of said biologically active protein is provided by an enzyme.

19. The process of claim 18 wherein the enzyme is provided by trypsin.

* * * * *